US007736302B2

(12) United States Patent
Matsuno

(10) Patent No.: US 7,736,302 B2
(45) Date of Patent: Jun. 15, 2010

(54) CAP FOR ENDOSCOPE

(75) Inventor: Kiyotaka Matsuno, Sagamihara (JP)

(73) Assignee: Olympus Corporation, Tokyo (JP)

( * ) Notice: Subject to any disclaimer, the term of this patent is extended or adjusted under 35 U.S.C. 154(b) by 102 days.

(21) Appl. No.: 11/439,807

(22) Filed: May 24, 2006

(65) Prior Publication Data
US 2006/0270906 A1   Nov. 30, 2006

Related U.S. Application Data

(63) Continuation of application No. PCT/JP2004/017588, filed on Nov. 26, 2004.

(30) Foreign Application Priority Data
Nov. 26, 2003   (JP)   ............................ P2003-395193

(51) Int. Cl.
A61B 1/04 (2006.01)
A61B 1/12 (2006.01)
A61B 10/00 (2006.01)
(52) U.S. Cl. ....................... 600/127; 600/129; 600/156; 600/565
(58) Field of Classification Search ................. 600/127, 600/153, 156, 175, 565; 604/256
See application file for complete search history.

(56) References Cited

U.S. PATENT DOCUMENTS 5,695,448 A * 12/1997 Kimura et al. .............. 600/121
6,306,081 B1 * 10/2001 Ishikawa et al. ............ 600/127
6,338,345 B1 * 1/2002 Johnson et al. ............. 128/897
6,524,234 B2 * 2/2003 Ouchi ........................ 600/127
6,858,014 B2 * 2/2005 Damarati .................... 600/565
2001/0053909 A1 12/2001 Nakada et al.
2003/0191413 A1 10/2003 Damarati

FOREIGN PATENT DOCUMENTS

| JP | 55-84141 | 6/1980 |
|----|----------|--------|
| JP | 11-4799 | 1/1999 |
| JP | 2001-258822 | 9/2001 |
| JP | 2002-45369 | 2/2002 |
| JP | 2003-204921 | 7/2003 |

OTHER PUBLICATIONS

Kumai, Koichiro, "Decision Tree of Diagnosis and Treatment of Bleeding in Digestive Organs," Digestive Organ Endoscopes, Digestive Organ Endoscope Editorial Committee, Tokyo Medical Co. Ltd., Feb. 25, 2003, vol. 15, No. 2 (Together with partial English-language translation).

* cited by examiner

Primary Examiner—Linda C Dvorak
Assistant Examiner—Alireza Nia
(74) Attorney, Agent, or Firm—Scully, Scott, Murphy & Presser, P.C.

(57) ABSTRACT

A cap for an endoscope includes: a cylindrical portion formed so that a distal end thereof protrudes forwardly from a distal end of an insertion portion of an endoscope; and a suction path that is connected to a suction device, and that communicates with an internal surface of the cylindrical portion.

6 Claims, 3 Drawing Sheets

CAP FOR ENDOSCOPE

PRIORITY CLAIM

This application is continuation application of a PCT Application No. PCT/JP2004/017588, filed on Nov. 26, 2004, entitled "CAP FOR ENDOSCOPE" whose priority is claimed on Japanese Patent Application No. 2003-395193, filed Nov. 26, 2003. The contents of which are incorporated herein by reference.

BACKGROUND OF THE INVENTION

1. Field of the Invention

The present invention relates to a cap for an endoscope.

2. Description of Related Art

If hemorrhaging occurs from a digestive tract then an endoscopic method is selected first as the method of hemostasis. When implementing this endoscopic hemostasis, it is vital that a search is made of the point of the hemorrhaging. Conventionally, the point of hemorrhage is looked for by changing the physical posture of the patient so that congealed blood and blood that has hemorrhaged inside the digestive tract is moved, or by using the water supply function of an endoscope to discharge jets of water so that the hemorrhaged blood and congealed blood is washed away, or by using the suction function of an endoscope to suction hemorrhaged blood or congealed blood from the large intestinal tract (see, for example, "Decision Tree of Diagnosis and Treatment of Bleeding in Digestive Organs", by Koichiro Kumai, Digestive Organ Endoscopes, Digestive Organ Endoscope Editorial Committee, Tokyo Medical Co. Ltd., Feb. 25, 2003, Vol. 15, No. 2)

The present invention was conceived in view of the above circumstances and it is an object thereof to provide a cap for an endoscope that makes it possible to accurately ascertain a point of hemorrhage without suctioning up a greater quantity of blood than is necessary, and that can be used in endoscopic hemostasis to allow immediate hemostasis.

SUMMARY OF THE INVENTION

A cap for an endoscope according to a first aspect of the present invention, includes: a cylindrical portion formed so that a distal end thereof protrudes forwardly from a distal end of an insertion portion of an endoscope; and a suction path that is connected to a suction device, and that communicates with an internal surface of the cylindrical portion.

A cap for an endoscope according to a second aspect of the present invention, includes: a cylindrical member having a base end which is removably fitted onto an insertion portion of an endoscope; and a suction path whose distal end is positioned between a distal end of the cylindrical member and a distal end of the insertion portion, and whose base end is connectable to a suction source, when the cylindrical member is attached to the insertion portion.

DESCRIPTION OF THE PREFERRED EMBODIMENTS

The first embodiment of the present invention will now be described with reference made to FIGS. 1 and 2.

Figure 1:
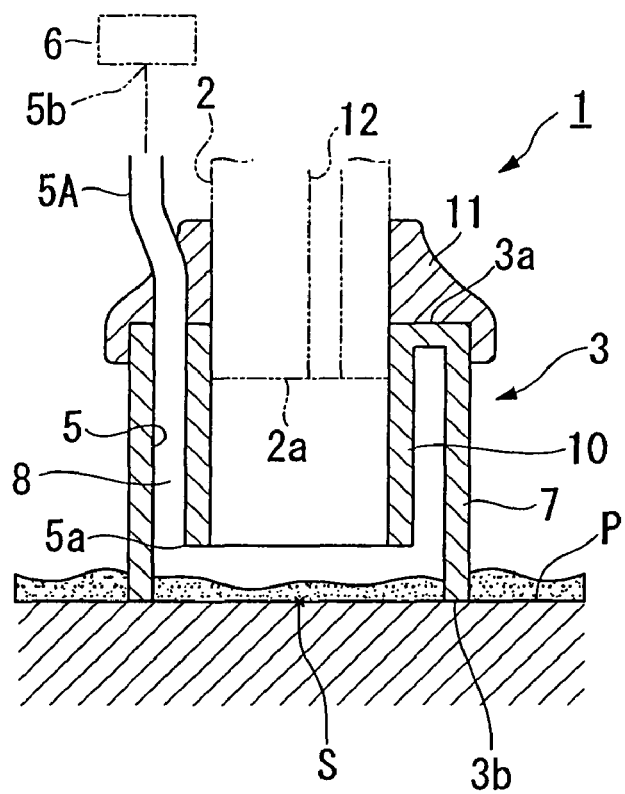
FIG. 1 is a cross-sectional view showing a cap for an endoscope according to a first embodiment of the present invention.
Figure 2:
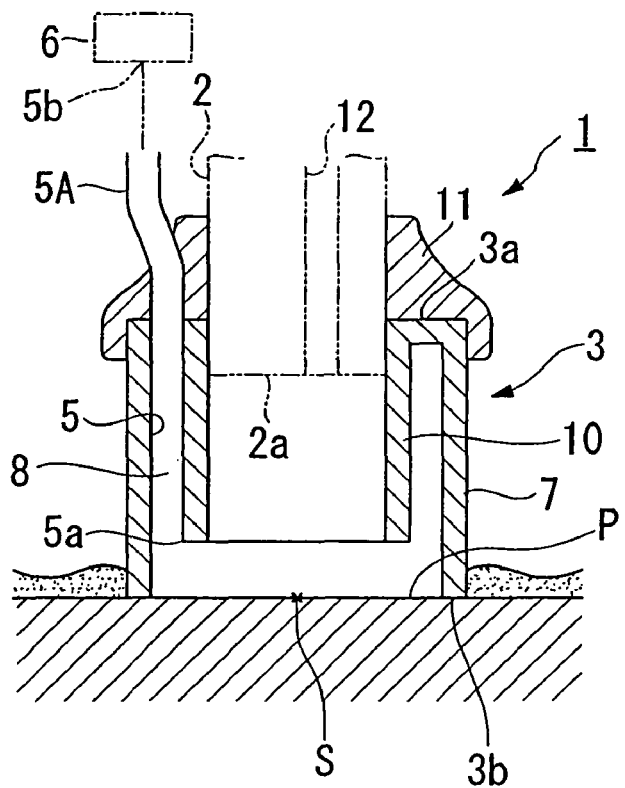
FIG. 2 is also a cross-sectional view showing a cap for an endoscope according to the first embodiment of the present invention and shows a state after blood has been suctioned.

As is shown in FIGS. 1 and 2, a cap for an endoscope 1 of the present embodiment is removably fitted onto a distal end of an insertion portion 2 of an endoscope. The cap for an endoscope 1 is formed by an annular fitting member 11 and a cylindrical member 3.

The fitting member 11 is made of a flexible material that is elastically deformable and is fitted onto the insertion portion 2 by inserting a distal end 2a of the insertion portion 2 into the fitting member 11 so that the fitting member 11 is tightly fitted onto the exterior surface of the insertion portion 2.

The cylindrical member 3 is made of a transparent material that may be formed, for example, from an acrylic, a polycarbonate, a polyolefin based elastomer, or the like. The cylindrical member 3 has a dual structure that is formed by a cylindrical outer cylindrical portion (i.e., a cylindrical portion) 7 and inner cylindrical portion 10 that have the same center. A base end 3a of the cylindrical member 3 is joined to the fitting member 11 such that the center of the cylindrical member 3 matches the center of the fitting member 11.

When the fitting member 11 has been fitted onto the insertion portion 2, the distal end 2a of the insertion portion 2 is inserted part of the way into the interior side of the inner cylindrical portion 10. When the outer cylindrical portion (i.e., the cylindrical portion) 7 and the inner cylindrical portion 10 are fitted onto the insertion portion 2, they both protrude forward of the distal end 2a of the insertion portion 2 and are formed so as to envelop the distal end 2a of the insertion portion 2. However, the length of this protruding portion of the inner cylindrical portion 10 is slightly shorter than the length of the protruding portion of the outer cylindrical portion 7.

A suction path 5 that is connected to a suction source (i.e., a suction device) 6 is formed so as to pass through a gap 8 between the outer cylindrical portion 7 and the inner cylindrical portion 10 in the cylindrical member 3. When viewed from the axial direction of the cylindrical member 3, the gap 8 is formed in the shape of a circular groove, and the suction path 5 opens onto a bottom surface thereof. Namely, the gap 8 performs the role of a suction port for the suction path 5. For example, a cylinder that is manually operated or a suction pump having a drive source or the like may be employed for the suction source 6 that is connected via a flexible tube member 5A to the suction path 5.

Next, a method of using the cap for an endoscope 1 of the present embodiment as well as the operation and effects thereof will be described.

Firstly, the cap for an endoscope 1 is fitted to the insertion portion 2 of an endoscope by inserting the distal end 2a of the insertion portion 2 inside the fitting portion 11. Next, the suction path 5 is connected via the tube member 5A to the suction source 6. In this state, the insertion portion 2 of the endoscope is inserted into a body cavity and the distal end 2a thereof is brought to the proximity of the area affected by the hemorrhaging.

As is shown in FIG. 1, a surface P of biomedical tissue that includes a hemorrhage point S is then covered by the outer cylindrical portion 7 by either pressing a distal end 3b of the outer cylindrical portion 7 onto the biomedical tissue or by applying suction via the suction path 5 so that the distal end 3b of the outer cylindrical portion 7 becomes adhered to the surface P of the biomedical tissue. At this time, even though the distal end 3b of the outer cylindrical portion 7 is adhered to the surface P of the biomedical tissue, because of the difference in the lengths of the outer cylindrical portion 7 and the inner cylindrical portion 10, the distal end 5a of the outer cylindrical portion 10 does not become adhered to the surface P of the biomedical tissue, but faces the surface P of the biomedical tissue with a gap between the two.

Next, suction is started by operating the suction source 6. When this suction is started, both blood and air are cleared away from the interior side of the cylindrical member 3. Therefore, the distal end 3b of the outer cylindrical portion 7 adheres to the surface P of the biomedical tissue and the flow of air and blood from the exterior side of the cylindrical member 3 to the interior side thereof is blocked. As a result, the blood on the interior side of the cylindrical member 3 is removed quickly and, as is shown in FIG. 2, the hemorrhage point S is exposed. Once the hemorrhage point S has been exposed, a hemostasis treatment tool is inserted into a channel 12 that is provided in the insertion portion 2, and is made to protrude from the distal end 2a of the insertion portion 2 so as to perform a predetermined hemostasis treatment.

In the cap for an endoscope 1 of the present embodiment, because the distal end 3b of the outer cylindrical portion 7 is pressed against the surface P of the biomedical tissue surrounding the hemorrhage point S so that the hemorrhage point S is completely isolated from the surrounding area by the outer cylindrical portion 7, there is no flow of blood from the surrounding area to the hemorrhage point S even when the blood on the interior side of the outer cylindrical portion 7 is suctioned via the suction path 5. Accordingly, there is no suctioning of blood beyond what is necessary and efficiency is excellent.

Moreover, because blood does not flow from the surrounding area to the hemorrhage point S, the hemorrhage point S does not become concealed by blood after the suctioning has ended and an excellent visual field is ensured. Accordingly, the hemorrhage point S can be accurately ascertained, and hemostasis can be immediately and reliably performed.

Moreover, in the cap for an endoscope 1 of the present embodiment, as a result of the protrusion length of the inner cylindrical portion 10 being slightly shorter than the protrusion length of the outer cylindrical portion 7, and as a result of the suction path 5 being connected to the gap 8 between the outer cylindrical portion 7 and the inner cylindrical portion 10, even if a bulge arises in the surface P of the biomedical tissue so that it comes into contact with the gap 8, only a portion of the gap 8 is blocked and a portion of the gap 8 always remains open. Accordingly, even if a bulge arises in the surface P of the biomedical tissue, the blood is not allowed to accumulate and can be suctioned in a stable manner.

Furthermore, in the cap for an endoscope 1 of the present embodiment, the gap 8 between the outer cylindrical portion 7 and the inner cylindrical portion 10 is formed in an annular shape, and when the distal end 3b of the outer cylindrical portion 7 is pressed against the surface P of the biomedical tissue surrounding the hemorrhage point S, the aperture of the gap 8 is positioned adjacent to the surface P of the biomedical tissue. As a result, the negative pressure of the suction source 6 acts effectively on the blood, and the blood is suctioned from around the hemorrhage point S along the interior surface of the outer cylindrical portion 7. Therefore, the blood can be suctioned in a stable manner without being obstructed by any bulging of the biomedical tissue.

If a distal end of the channel 12 and a lens (not shown) are located at the distal end 2a of the insertion portion 2 of the endoscope, then if suction is applied via the channel 12, the negative pressure acts on the surface P of the biomedical tissue facing the channel 12 and the surface P of the biomedical tissue is made to bulge out towards the lens surface adjacent to the channel 12. As a result, there is a possibility that the visual field of the endoscope will become obstructed. However, in the cap for an endoscope 1 of the present embodiment, because the negative pressure acts along the inner circumferential surface of the outer cylindrical portion 7 and the surface P of the biomedical tissue is pulled so as to spread peripherally outwards instead of bulging towards the lens surface, there is no obstruction of the visual field.

Moreover, because the distance between the distal end 2a of the endoscope insertion portion 2 and the biomedical tissue surface P is kept at a predetermined length by the cylindrical member 3 that has been placed on the distal end 2a of the endoscope insertion portion 2, an excellent visual field is constantly maintained. As a result, it is possible to suction blood while observing the operation using an endoscope. Furthermore, because there is no bulging of the biomedical tissue surface P even after the removal of the blood has ended, hemostasis treatment can be performed immediately and accurately.

In the cap for an endoscope 1 of the present embodiment, because negative pressure is applied so as to encircle the hemorrhage point S so that, even if bumps and indentations or sloping portions occur on the biomedical tissue surface P on the interior side of the cylindrical member 3, the biomedical tissue surface P is tightly adhered without any break along the distal end 3b of the outer cylindrical portion 7, it is difficult for blood and air to enter from the outside of the cylindrical member 3 and extremely efficient suction of blood becomes possible.

In the cap for an endoscope 1 of the present embodiment, because the cylindrical member 3 is made from a transparent material, the hemorrhage point S and the area surrounding this can be viewed from the lens surface that is provided on the distal end 2a of the insertion portion 2 via the transparent cylindrical member 3. As a result, the surrounding area can be viewed even when the blood is being suctioned. Moreover, because the cap for an endoscope 1 of the present embodiment can be removably fitted onto the distal end 2a of the insertion portion 2, its general applicability can be improved by attaching it to an existing endoscope. Accordingly, it is not necessary for a new endoscope to be purchased, which is clearly economically advantageous.

Next, the second embodiment of the present invention will be described with reference made to FIGS. 3 and 4. Note that component elements that are the same as those in the above described first embodiment are given the same symbols and a description thereof is omitted.

In the cap for an endoscope 1 of the first embodiment, the cylindrical member 3 has a dual structure that is formed by the outer cylindrical portion 7 and the inner cylindrical portion 10, and the suction path 5 is connected to a gap 8 between the outer cylindrical portion 7 and the inner cylindrical portion 10 so that the gap 8 performs the role of a suction port for the suction path 5. In contrast, as is shown in FIGS. 3 and 4, in the cap for an endoscope 13 of the second embodiment, a distal end of a tube member 15A protrudes from a suction path 15 onto an inner side of a cylindrical member 16. The cylindrical member 16 has a single layer structure that is formed by the outer cylindrical portion 7 only, and is removably fitted onto the insertion portion 2 using a fitting portion 11 that is joined to a distal end 16a of the cylindrical member 16.

By using the cap for an endoscope 13 of the present embodiment in the same way as the cap for an endoscope of the first embodiment, the same operation and effects can be obtained.

Figure 3:
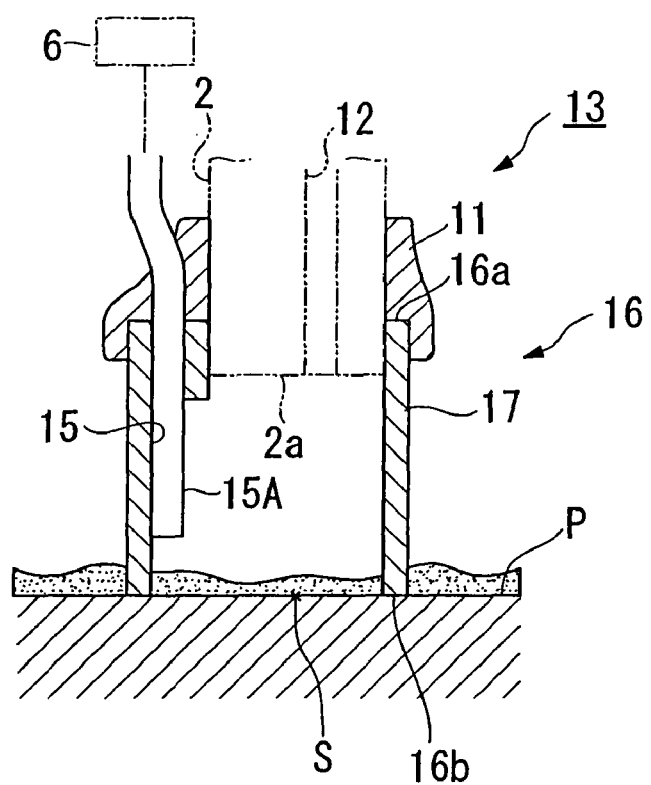
FIG. 3 is a cross-sectional view showing a cap for an endoscope according to a second embodiment of the present invention.
Figure 4:
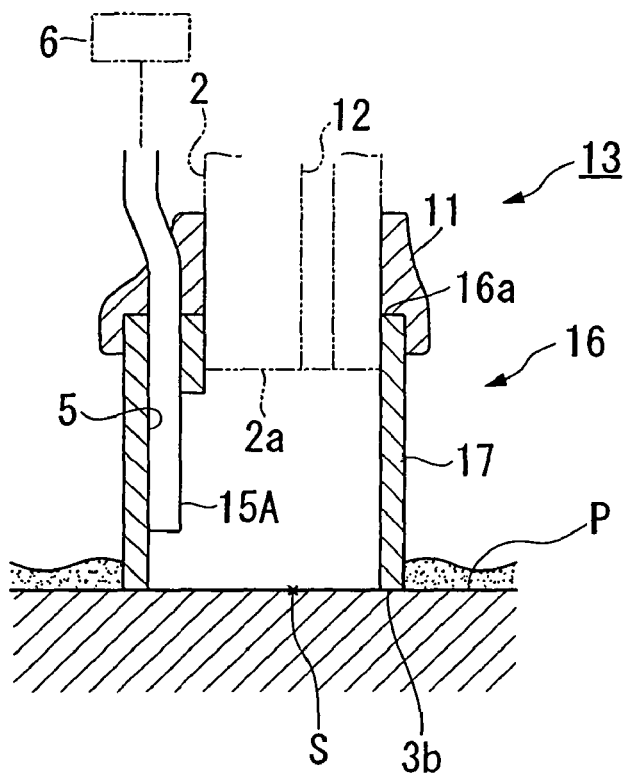
FIG. 4 is also a cross-sectional view showing a cap for an endoscope according to the second embodiment of the present invention and shows a state after blood has been suctioned.

Namely, as is shown in FIG. 3, a distal end 16b of the outer cylindrical portion 7 is pressed against the hemorrhaging biomedical tissue surface P, and blood that has hemorrhaged from the hemorrhage point S is suctioned from the distal end of the tube member 15A. As a result, as is shown in FIG. 4, it is possible to suction only the blood that is inside the outer cylindrical portion 7.

At this time, it is possible to concentrate the blood at the distal end of the tube member 15A so that it can be efficiently suctioned. Moreover, because the cylindrical member 16 does not have a dual structure, but has a single layer structure formed by the outer cylindrical portion 7 only, an even broader visual field can be ensured for the endoscope.

Note that in the cap for an endoscope 13 of the present embodiment, the distal end of the tube member 15A may be split into a plurality of branches, and the split distal ends may be positioned at intervals from each other in the inner circumferential direction of the outer cylindrical portion 7.

Next, the third embodiment of the present invention will be described with reference made to FIG. 5. Note that component elements that are the same as those in the above described embodiments are given the same symbols and a description thereof is omitted.

Figure 5:
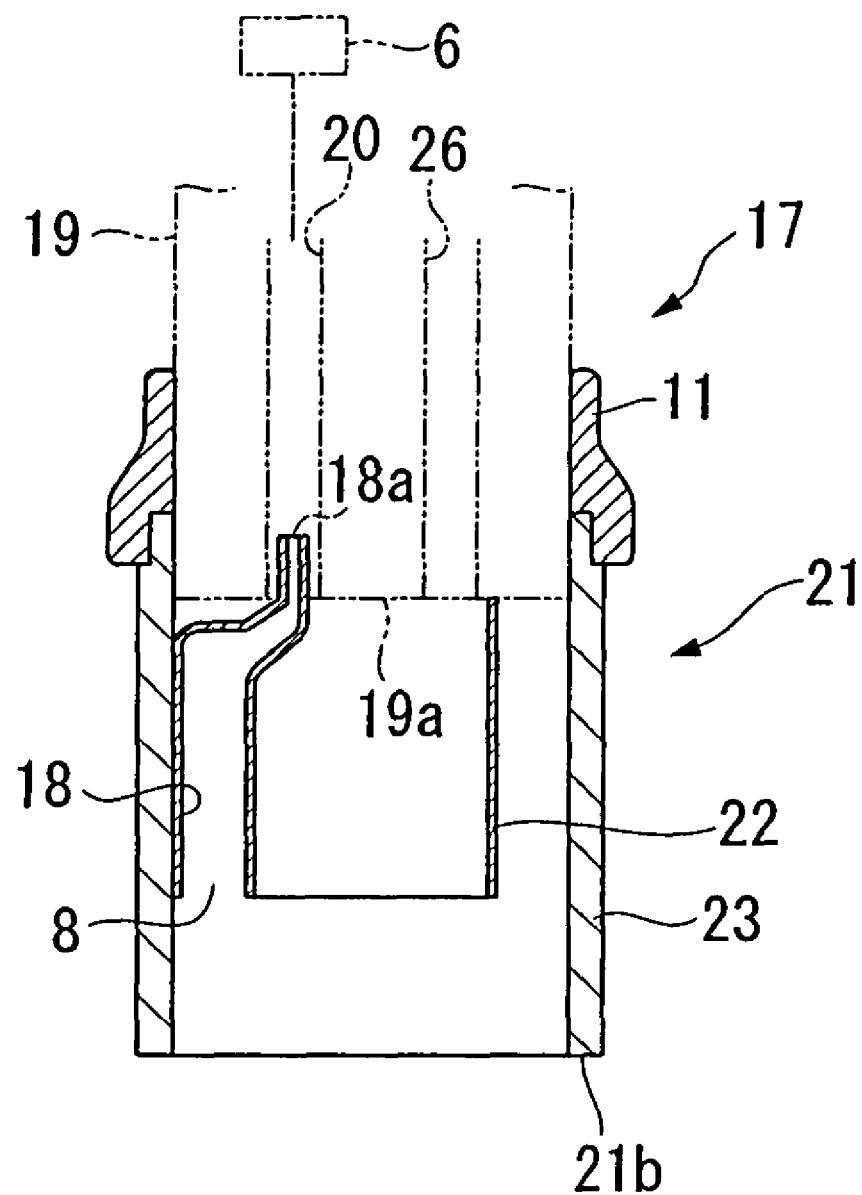
FIG. 5 is a cross-sectional view showing a cap for an endoscope according to a third embodiment of the present invention.

In a cap for an endoscope 17 of the third embodiment, as is shown in FIG. 5, a suction path 18 can be connected to a suction channel 20 that is provided in an insertion portion 19.

The cylindrical member 21 has a dual structure that is formed by an outer cylindrical portion 23 and an inner cylindrical portion 22 that are both independent members. The inner diameter of the outer cylindrical portion 23 is substantially equal to the outer diameter of a distal end 19a of the insertion portion 19, and the outer diameter of the inner cylindrical portion 22 is formed smaller than the outer diameter of the distal end 19a of the insertion portion 19. When the fitting member 11 is fitted to the insertion portion 19, the distal end 19a of the insertion portion 19 is inserted partway into the inner side of the outer cylindrical portion 23 and comes into contact with the base end of the inner cylindrical portion 22. The inner cylindrical portion 22 is positioned such that the suction channel 20 and another channel 26 are contained on an inner side thereof.

The suction path 18 is formed on an outer side surface of the inner cylindrical portion 22. The suction path 18 is connected to the gap 8 between the outer cylindrical portion 23 and the inner cylindrical portion 22 so that the gap 8 performs the role of a suction port for the suction path 18. A base end 18a of the suction path 18 extends towards the fitting member 11 and is bent so as to form a crank on the inner side of the inner cylindrical portion 22. When the fitting member 11 is fitted onto the insertion portion 19, the base end 18a of the suction path 18 gets inserted into the insertion channel 20.

By using the cap for an endoscope 17 of the present embodiment as well in the same way as the cap for an endoscope of the first embodiment, the same operation and effects can be obtained.

Namely, as is shown in FIG. 5, by pressing the distal end 21b of the outer cylindrical portion 23 against the hemorrhaging biomedical tissue surface P and then suctioning the blood that has hemorrhaged from the hemorrhage point S from the gap 8 via the suction channel 20, it is possible to suction only the blood on the inner side of the outer cylindrical portion 23.

According to the cap for an endoscope of the present embodiment, by connecting the suction path 18 to the suction channel 20 that is provided in the insertion portion 19, there is no need to provide a conduit for suction separately from the insertion portion 19. As a result, the burden on a patient when the insertion portion 19 is being inserted can be alleviated. In addition, by using the suction channel 20 to suction blood and using the other channel 26 for hemostasis treatment that uses a treatment tool, the procedure can be completed without imposing any burden on the patient.

In the cap for an endoscope of the present invention, if the distal end of the insertion portion of an endoscope to which the cap for an endoscope of the present invention has been fitted is pressed against a hemorrhage point, the distal end of the cylindrical portion of the cap for an endoscope is placed against the surface of the biomedical tissue surrounding the hemorrhage point, and the hemorrhage point is isolated from the surrounding area by the cylindrical portion. As a result, even if blood on the interior side of the cylindrical portion is suctioned via the suction path, no blood flows from the surrounding area to the hemorrhage point. Accordingly, there is no suctioning of blood beyond what is necessary and efficiency is excellent.

Moreover, because blood does not flow from the surrounding area to the hemorrhage point, the hemorrhage point does not become concealed by blood after the suctioning has ended and an excellent visual field is ensured. Accordingly, the hemorrhage point can be accurately ascertained, and hemostasis can be immediately and reliably performed.

According to the cap for an endoscope of the present invention, by making the length of the protruding portion of the inner cylindrical portion shorter than the length of the protrusion of the cylindrical portion, and by making the suction path communicate with a gap between the cylindrical portion and the inner cylindrical portion, even if the surface of the biomedical tissue bulges outwards and makes contact with this gap, only a portion of the gap is blocked and there is no blocking of the entire gap. Accordingly, even if a bulge arises in the surface of the biomedical tissue, the blood is not allowed to accumulate and can be suctioned in a stable manner.

According to the cap for an endoscope of the present invention, by forming the gap between the cylindrical portion and the inner cylindrical portion in an annular shape, blood is suctioned from around the hemorrhage point along the interior surface of the cylindrical portion. Therefore, the blood can be suctioned in a stable manner without being obstructed by any bulging of the biomedical tissue.

According to the cap for an endoscope of the present invention, by connecting the suction path to a suction channel that is provided in the insertion portion, there is no need to provide a conduit for suction separately from the insertion portion. In the case of an endoscope that has two channels provided in the insertion portion, by using one channel to suction blood and the other channel for hemostasis treatment that uses a treatment tool, the procedure can be completed without imposing any burden on the patient.

According to the cap for an endoscope of the present invention, because the area surrounding the hemorrhage point can be viewed from the distal end of the insertion portion via the transparent cylindrical portion, the surrounding area can be observed even when the blood is being suctioned.

According to the cap for an endoscope of the present invention, by attaching this cap for an endoscope to an existing endoscope, its general applicability can be improved and it is not necessary for a new endoscope to be purchased, which is economically advantageous.

According to the cap for an endoscope of the present invention, because it is possible to accurately ascertain a hemorrhage point without suctioning a greater quantity of blood than is absolutely necessary, if this cap for an endoscope is used for endoscopic hemostasis, rapid hemostasis becomes possible.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as limited by the foregoing description and is only limited by the scope of the appended claims.

The present invention relates to a cap for an endoscope that is fitted onto a distal end of an insertion portion of an endoscope, and includes: a cylindrical portion that protrudes forwardly from the distal end of the insertion portion and is formed so as to surround the distal end of the insertion portion; and a suction path that communicates with an interior side of the cylindrical portion and is connected to a suction device. According to the cap for an endoscope of the present invention, because it is possible to accurately ascertain a hemorrhage point without suctioning a greater quantity of blood than is absolutely necessary, if this cap for an endoscope is used for endoscopic hemostasis, rapid hemostasis becomes possible.

What is claimed is:

1. A cap for an endoscope which is allowed to be fitted onto a distal end of an insertion portion of the endoscope, the cap comprising:
   a cylindrical portion formed so that a distal end thereof protrudes forwardly from the distal end of the insertion portion in a state where the cap is fitted onto the distal end of the insertion portion;
   a first opening adapted to be pressed onto a biomedical tissue surface, which is formed at the distal end of the cylindrical portion;
   a suction path that is connectable to a suction device;
   an inner cylindrical portion formed inside the cylindrical portion so that a distal end thereof protrudes forwardly from the distal end of the insertion portion; and
   a second opening formed at the distal end of the inner cylindrical portion so as to face in the same direction of the first opening; wherein
   the length of the inner cylindrical portion protruding from the distal end of the insertion portion is shorter than the length of the cylindrical portion protruding from the distal end of the insertion portion, and
   a gap is arranged between the inside surface of the cylindrical portion and the outside surface of the inner cylindrical portion; and
   the suction path directly communicates with only the gap at a portion closer to a proximal end of the insertion portion than the second opening of the inner cylindrical portion.

2. The cap according to claim 1, wherein the suction path is connectable to a suction channel that is provided in the insertion portion of the endoscope.

3. The cap according to claim 1, wherein at least the cylindrical portion is made of a transparent material.

4. The cap according to claim 1, wherein the cap is removably fitted onto the distal end of the insertion portion.

5. The cap according to claim 1,
   wherein the distal end of the cylindrical member fitted onto the insertion portion is pressed onto the biomedical tissue surface, and thereafter
   a biological fluid inside the cylindrical member is suctioned via the gap and the suction path while performing a treatment procedure by the endoscope.

6. The cap according to claim 1, wherein the suction path is connected to the suction device via a tube member that is arranged outside the insertion portion.

* * * * *